United States Patent
Jones et al.

(10) Patent No.: US 11,617,772 B2
(45) Date of Patent: Apr. 4, 2023

(54) NUTRITIONAL SUPPLEMENTS AND THERAPEUTIC COMPOSITIONS COMPRISING PROBIOTICS

(71) Applicant: Direct Digital, LLC, Charlotte, NC (US)

(72) Inventors: Natalie Jones, Charlotte, NC (US); Mikala Hukka, Charlotte, NC (US)

(73) Assignee: Direct Digital LLC, Charlotte, NC (US)

(*) Notice: Subject to any disclaimer, the term of this patent is extended or adjusted under 35 U.S.C. 154(b) by 498 days.

(21) Appl. No.: 16/566,150

(22) Filed: Sep. 10, 2019

(65) Prior Publication Data

US 2020/0078421 A1 Mar. 12, 2020

Related U.S. Application Data

(60) Provisional application No. 62/729,811, filed on Sep. 11, 2018.

(51) Int. Cl.

| | |
|---|---|
| *A61K 35/747* | (2015.01) |
| *A61K 35/745* | (2015.01) |
| *A61K 31/197* | (2006.01) |
| *A61K 36/84* | (2006.01) |
| *A61K 31/4045* | (2006.01) |
| *A23L 33/135* | (2016.01) |
| *A23L 33/175* | (2016.01) |
| *A23L 33/105* | (2016.01) |
| *A61K 31/20* | (2006.01) |
| *A61K 47/12* | (2006.01) |
| *A61K 47/02* | (2006.01) |

(52) U.S. Cl.
CPC .......... *A61K 35/747* (2013.01); *A23L 33/105* (2016.08); *A23L 33/135* (2016.08); *A23L 33/175* (2016.08); *A61K 31/197* (2013.01); *A61K 31/20* (2013.01); *A61K 31/4045* (2013.01); *A61K 35/745* (2013.01); *A61K 36/84* (2013.01); *A61K 47/02* (2013.01); *A61K 47/12* (2013.01)

(58) Field of Classification Search
CPC ................ A61K 35/747; A61K 35/745; A23L 33/175; A23L 33/105; A23L 33/135
See application file for complete search history.

(56) References Cited

U.S. PATENT DOCUMENTS

| | | |
|---|---|---|
| 2007/0014719 A1 | 1/2007 | Reading et al. |
| 2007/0207134 A1 | 9/2007 | Moriyama et al. |
| 2012/0034193 A1 | 2/2012 | Rees et al. |
| 2014/0017337 A1 | 1/2014 | Amoruso |
| 2014/0144429 A1 | 5/2014 | Wensley et al. |
| 2014/0308374 A1 | 10/2014 | Goel |
| 2015/0125548 A1 | 5/2015 | Knutsen et al. |
| 2015/0216237 A1 | 8/2015 | Wensley et al. |
| 2015/0367366 A1 | 12/2015 | Edwards et al. |
| 2016/0263047 A1 | 9/2016 | Kaufman |

FOREIGN PATENT DOCUMENTS

| | | | |
|---|---|---|---|
| CN | 106071436 A | | 11/2016 |
| EP | 2717890 | * | 4/2014 |
| IN | 27/2010 | | 7/2010 |
| WO | 2013133903 A1 | | 9/2013 |
| WO | WO 2014/151329 | * | 9/2014 |
| WO | 2017180587 A2 | | 10/2017 |

OTHER PUBLICATIONS

Amazon website product page, reviews page for Peptiva + Sleep Support (Year: 2017).*
Rades, T., Perrie, Y. (2012). Pharmaceutics: Drug Delivery and Targeting. United Kingdom: Pharmaceutical Press., chapter 1 (Year: 2012).*
Bull et al., "The domestication of the probiotic bacterium Lactobacillus acidophilus", Scientific Reports (4 : 7202) DOI: 10.1038/srep07202 (Year: 2014).*
https://en.wikipedia.org/wiki/Lactobacillus_acidophilus (Year: 2022).*
Laurel Vukovic; "The Power Of Sleep"; Better Nutrition; https://www.betternutrition.com/features-dept/insomnia-sleep-caffeine-herbs; Apr. 1, 2010; 2 pages.
PRWeb; "Nutri-Health Supplements Adds Sleep Wave—A Natural Sleep Support Formula—To Its Premium Product Line"; https://www.prweb.com/releases/2011/7/prweb8665144.htm; Jul. 26, 2011; 3 pages.
Douglas Lobay; "GABA in the treatment of anxiety"; gamma aminobutyric acid; Townsend Letter; Oct. 1, 2016; https://www.thefreelibrary.com/GABA+in+the+treatment+of+anxiety.-a0465198862; 7 pages.
Nunez, K.; "How Long Melatonin Remains in Your Body, Efficacy, and Dosage Tips"; Sep. 11, 2019; https://www.healthline.com/health/how-long-does-melatonin-last.

* cited by examiner

*Primary Examiner* — Ruth A Davis
(74) *Attorney, Agent, or Firm* — Jeffri A. Kaminski; Venable LLP

(57) ABSTRACT

Disclosed herein are therapeutic compositions and nutritional supplements comprising probiotic mixtures and sleep-support ingredients, and a method of treating digestive discomfort and sleep problems comprising administering an effective amount of a therapeutic composition comprising a probiotic component and a sleep support component. According to embodiments, therapeutic compositions for improved digestion are provided comprising: a probiotic component, comprising: at least one of *Lactobacillus acidophilus*, *Bifidobacterium bifidum*, *Bifidobacterium animalis*, *Lactobacillus rhamnosus*, and *Lactobacillus paracasei*; and a sleep support component, comprising: at least one of gamma-aminobutyric acid (GABA), valerian root extract, and melatonin. The therapeutic compositions are effective in treating both sleep disorders and digestive discomfort.

16 Claims, No Drawings

NUTRITIONAL SUPPLEMENTS AND THERAPEUTIC COMPOSITIONS COMPRISING PROBIOTICS

BACKGROUND

Many people suffer from digestive discomfort and irregularity. In addition to the daily inconvenience, often digestive problems prevent restful sleep, which is a further disruption to daily life. What is needed is a natural and safe therapeutic composition that provides more than just temporary relief to daily digestive discomfort, and provides additional health benefits including sleep support.

SUMMARY

According to embodiments, therapeutic compositions and nutritional supplements are provided, comprising probiotic mixtures and sleep-support ingredients, and a method of treating digestive discomfort and sleep problems comprising administering an effective amount of a therapeutic composition comprising a probiotic component and a sleep support component.

According to another embodiment, therapeutic compositions for improved digestion are provided, comprising: a probiotic component, comprising: at least one of *Lactobacillus acidophilus, Bifidobacterium bifidum, Bifidobacterium animalis, Lactobacillus rhamnosus*, and *Lactobacilus paracasei*; and a sleep support component, comprising: at least one of gamma-aminobutyric acid (GABA), valerian root extract, and melatonin.

According to another embodiment, compositions for improved digestion are provided, comprising: a probiotic component comprising: *Lactobacillus acidophilus, Bifidobacterium bifidum, Bifidobacterium animalis* subsp. *lactis, Lactobacillus rhamnosus*, and *Lactobacillus paracasei*; gamma-aminobutyric acid (GABA), valerian root extract, and melatonin.

According to embodiments, compositions for improving digestion are provided, comprising: a clinical culture blend comprising: *Lactobacillus acidophilus* (ATCC SD6865), *Lactobacillus acidophilus* (ATCC SD6866), *Bifidobacterium bifidum* (ATCC SD6869), and *Bifidobacterium animalis* subsp. *lactis* (ATCC SD6870); an active microbiome blend comprising: *Lactobacillus rhamnosus* (IMC 501), and *Lactobacillus paracasei* (IMC 502); gamma-aminobutyric acid (GABA); valerian root extract; immediate release melatonin; and delayed release melatonin.

According to another embodiment, methods for improving digestion are provided, comprising administering to an individual an effective dose of a composition comprising: *Lactobacillus acidophilus, Bifidobacterium bifidum, Bifidobacterium animalis* subsp. *lactis, Lactobacillus rhamnosus, Lactobacillus paracasei*, gamma-aminobutyric acid (GABA), valerian root extract, and melatonin.

DETAILED DESCRIPTION

Described herein are nutritional supplements comprising probiotic mixtures and sleep-support ingredients, and methods of treating digestive discomfort and sleep problems comprising administering an effective amount of a therapeutic composition comprising a probiotic component and a sleep support component.

In one aspect, described herein a therapeutic composition comprising: a probiotic component, and a sleep support component.

In some embodiments, the probiotic component comprises at least one strain of *Lactobacillus*. In some embodiments, the probiotic component comprises at least one strain of *Bifidobacterium*. In some embodiments, the *Lactobacillus* is selected from the species *Lactobacillus acidophilus, Lactobacillus casei, Lactobacillus kefiri, Lactobacillus bifidus, Lactobacillus brevis, Lactobacillus helveticus, Lactobacillus paracasei, Lactobacillus rhamnosus, Lactobacillus salivarius, Lactobacillus curvatus, Lactobacillus bulgaricus, Lactobacillus sakei, Lactobacillus reuteri, Lactobacillus fermentum, Lactobacillus farciminis, Lactobacillus lactis, Lactobacillus delbreuckii, Lactobacillus plantarum, Lactobacillus paraplantarum, Lactobacillus crispatus, Lactobacillus gasseri, Lactobacillus johnsonii* and *Lactobacillus jensenii*, and combinations of any thereof. In some embodiments, the *Lactobacillus* may include ATCC SD6865, ATCC SD6866, CUL60, CUL20, IMC 501, IMC 502, and combinations thereof.

In some embodiments, the *Bifidobacterium* is selected from the species *Bifidobacterium lactis, Bifidobacterium bifidium, Bifidobacterium longum, Bifidobacterium animalis, Bifidobacterium animalis* subsp. *lactis, Bifidobacterium breve, Bifidobacterium infantis, Bifidobacterium catenulatum, Bifidobacterium pseudocatenulatum, Bifidobacterium adolescentis*, and *Bifidobacterium angulatum*, and combinations of any thereof. In some embodiments, the *Bifidobacterium* may include ATCC SD6869, ATCC SD6870, CUL24, CUL20, and combinations of any thereof.

In some embodiments, the sleep support component comprises at least one of melatonin, 5-hydroxytryptophan, 5-hydroxytrypatmine, kava, chamomile, L-theanine, L-tryptophan, gamma-aminobutyric acid (GABA), valerian root extract, magnesium, vitamins, amino acids, and combinations of any thereof.

In another aspect, described herein is a nutritional supplement comprising:
  (a) a probiotic component;
  (b) a sleep support component;
  (c) at least one excipient; and
  (d) a capsule.

In some embodiments, the excipient may be a coloring agent. In some embodiments, the excipient may be a diluent. In some embodiments, the excipient may be a binder. In some embodiments, the excipient may be a granulating agent. In some embodiments, the excipient may be a bulking agent. In some embodiments, the excipient may be a disintegrant. In some embodiments, the excipient may be a glidant. In some embodiments, the excipient may be a flavorant. In some embodiments, the excipient is selected from sugars, starches, polymers, alkaline and/or alkali earth stearate, carbonate and/or sulfate, kaolin, silica, flavorants, and aromas, and combinations of any thereof. In some embodiments, the excipient may be lipophilic, polymeric, cellulosic or combinations of any thereof. In some embodiments, the excipient may be selected from lactose, magnesium stearate, sodium carbonate, microcrystalline cellulose, silica, titanium dioxide, and combinations of any thereof.

In yet another aspect, described herein is a method of treating digestive discomfort and sleep problems comprising: administering an effective amount of a therapeutic composition comprising a probiotic component and a sleep-support component.

Therapeutic Compositions

In one aspect, described herein is a therapeutic composition comprising:
  (a) a probiotic component; and
  (b) a sleep support component.

Probiotic Component

In some embodiments, the probiotic component contains *Lactobacillus, Bifidobacterium*, and combinations thereof. In some embodiments, the *Lactobacillus* is *Lactobacillus acidophilus, Lactobacillus rhamnosus, Lactobacillus paracasei*, and combinations of any thereof. In some embodiments, the *Lactobacillus* is *Lactobacillus acidophilus* ATCC SD6865, *Lactobacillus acidophilus* ATC SD6866, *Lactobacillus rhamnosus* IMC 501, *Lactobacillus paracasei* IMC 502, and combinations of any thereof. In some embodiments, the *Bifidobacterium* is *Bifidobacterium bifidum, Bifidobacterium animalis* subsp. *lactis*, and combinations thereof. In some embodiments, the *Bifidobacterium* is *Bifidobacterium bifidum* ATCC SD6869, *Bifidobacterium animalis* subsp. *lactis* ATCC ATCC SD6870, and combinations thereof.

In some embodiments, the amount of the probiotic component is about 0.05 B CFU/g, about 0.1 B CFU/g, about 0.2 B CFU/g, about 0.3 B CFU/g, about 0.4 B CFU/g, about 0.5 B CFU/g, about 0.6 B CFU/g, about 0.7 B CFU/g, about 0.8 B CFU/g, about 0.9 B CFU/g, about 1.0 B CFU/g, about 1.1 B CFU/g, about 1.2 B CFU/g, about 1.3 B CFU/g, about 1.4 B CFU/g, about 1.5 B CFU/g, about 1.6 B CFU/g, about 1.7 B CFU/g, about 1.8 B CFU/g, about 1.9 B CFU/g, about 2.0 B CFU/g, about 2.1 B CFU/g, about 2.2 B CFU/g, about 2.3 B CFU/g, about 2.4 B CFU/g, about 2.5 B CFU/g, about 2.6 B CFU/g, about 2.7 B CFU/g, about 2.8 B CFU/g, about 2.9 B CFU/g, about 3.0 B CFU/g, about 3.1 B CFU/g, about 3.2 B CFU/g, about 3.3 B CFU/g, about 3.4 B CFU/g, about 3.5 B CFU/g, about 3.6 B CFU/g, about 3.7 B CFU/g, about 3.8 B CFU/g, about 3.9 B CFU/g, about 4.0 B CFU/g, about 4.1 B CFU/g, about 4.2 B CFU/g, about 4.3 B CFU/g, about 4.4 B CFU/g, about 4.5 B CFU/g, about 4.6 B CFU/g, about 4.7 B CFU/g, about 4.8 B CFU/g, about 4.9 B CFU/g, or about 5.0 B CFU/g.

In some embodiments, the amount of the probiotic component is about 1 B CFU/g, about 2 B CFU/g, about 3 B CFU/g, about 4 B CFU/g, about 5 B CFU/g, about 6 B CFU/g, about 7 B CFU/g, about 8 B CFU/g, about 9 B CFU/g, about 10 B CFU/g, about 11 B CFU/g, about 12 B CFU/g, about 13 B CFU/g, about 14 B CFU/g, about 15 B CFU/g, about 16 B CFU/g, about 17 B CFU/g, about 18 B CFU/g, about 19 B CFU/g, about 20 B CFU/g, about 21 B CFU/g, about 22 B CFU/g, about 23 B CFU/g, about 24 B CFU/g, about 25 B CFU/g, about 26 B CFU/g, about 27 B CFU/g, about 28 B CFU/g, about 29 B CFU/g, about 30 B CFU/g, about 31 B CFU/g, about 32 B CFU/g, about 33 B CFU/g, about 34 B CFU/g, about 35 B CFU/g, about 36 B CFU/g, about 37 B CFU/g, about 38 B CFU/g, about 39 B CFU/g, about 40 B CFU/g, about 41 B CFU/g, about 42 B CFU/g, about 43 B CFU/g, about 44 B CFU/g, about 45 B CFU/g, about 46 B CFU/g, about 47 B CFU/g, about 48 B CFU/g, about 49 B CFU/g, or about 50 B CFU/g.

In some embodiments, the probiotic component comprises Lab4™ Clinical Cultures blend, an Active Microbiome Blend, or a combination thereof. In some embodiments, the Lab4™ Clinical Cultures blend contains *Lactobacillus acidophilus* ATCC SD6865, *Lactobacillus acidophilus* ATC SD6866, *Bifidobacterium bifidum* ATCC SD6869, *Bifidobacterium animalis* subsp. *lactis* ATCC SD6870, and combination thereof. According to embodiments, the Active Microbiome Blend contains *Lactobacillus rhamnosus* IMC 501, *Lactobacillus paracasei* IMC 502, and combinations of any thereof.

In some embodiments, Lab4™ Clinical Cultures blend is about 1 B CFU/g, about 2 B CFU/g, about 3 B CFU/g, about 4 B CFU/g, about 5 B CFU/g, about 6 B CFU/g, about 7 B CFU/g, about 8 B CFU/g, about 9 B CFU/g, about 10 B CFU/g, about 11 B CFU/g, about 12 B CFU/g, about 13 B CFU/g, about 14 B CFU/g, about 15 B CFU/g, about 16 B CFU/g, about 17 B CFU/g, about 18 B CFU/g, about 19 B CFU/g, about 20 B CFU/g, about 21 B CFU/g, about 22 B CFU/g, about 23 B CFU/g, about 24 B CFU/g, about 25 B CFU/g, about 26 B CFU/g, about 27 B CFU/g, about 28 B CFU/g, about 29 B CFU/g, about 30 B CFU/g, about 31 B CFU/g, about 32 B CFU/g, about 33 B CFU/g, about 34 B CFU/g, about 35 B CFU/g, about 36 B CFU/g, about 37 B CFU/g, about 38 B CFU/g, about 39 B CFU/g, about 40 B CFU/g, about 41 B CFU/g, about 42 B CFU/g, about 43 B CFU/g, about 44 B CFU/g, about 45 B CFU/g, about 46 B CFU/g, about 47 B CFU/g, about 48 B CFU/g, about 49 B CFU/g, or about 50 B CFU/g.

In some embodiments, the Active Microbiome Blend is about 0.05 B CFU/g, about 0.1 B CFU/g, about 0.2 B CFU/g, about 0.3 B CFU/g, about 0.4 B CFU/g, about 0.5 B CFU/g, about 0.6 B CFU/g, about 0.7 B CFU/g, about 0.8 B CFU/g, about 0.9 B CFU/g, about 1.0 B CFU/g, about 1.1 B CFU/g, about 1.2 B CFU/g, about 1.3 B CFU/g, about 1.4 B CFU/g, about 1.5 B CFU/g, about 1.6 B CFU/g, about 1.7 B CFU/g, about 1.8 B CFU/g, about 1.9 B CFU/g, about 2.0 B CFU/g, about 2.1 B CFU/g, about 2.2 B CFU/g, about 2.3 B CFU/g, about 2.4 B CFU/g, about 2.5 B CFU/g, about 2.6 B CFU/g, about 2.7 B CFU/g, about 2.8 B CFU/g, about 2.9 B CFU/g, about 3.0 B CFU/g, about 3.1 B CFU/g, about 3.2 B CFU/g, about 3.3 B CFU/g, about 3.4 B CFU/g, about 3.5 B CFU/g, about 3.6 B CFU/g, about 3.7 B CFU/g, about 3.8 B CFU/g, about 3.9 B CFU/g, about 4.0 B CFU/g, about 4.1 B CFU/g, about 4.2 B CFU/g, about 4.3 B CFU/g, about 4.4 B CFU/g, about 4.5 B CFU/g, about 4.6 B CFU/g, about 4.7 B CFU/g, about 4.8 B CFU/g, about 4.9 B CFU/g, or about 5.0 B CFU/g.

Sleep Support Component

In some embodiments, the sleep support component comprises at least one of melatonin, 5-hydroxytryptophan, 5-hydroxytrypatmine, kava, chamomile, L-theanine, L-tryptophan, gamma-aminobutyric acid (GABA), valerian root extract, magnesium, vitamins, amino acids, and combinations of any thereof. In some embodiment, the sleep support component is from a natural source. In some embodiments, the sleep support component is synthetic. In some embodiments, the sleep support component is a combination of natural source and synthetic. In some embodiments, the sleep support component comprises at least one of at least one of melatonin, gamma-aminobutyric acid (GABA), valerian root extract, and combinations of any thereof. In some embodiments, the GABA is PharmaGABA. In some embodiments, the sleep support components may be immediate release. In some embodiments, the sleep support component may be delayed release. In some embodiments, the sleep support components may be a combination of immediate release and delayed release. In some embodiments, the sleep support component may be immediate release melatonin, delayed release melatonin, GABA, valerian root extract, and combinations of any thereof.

In some embodiments, the amount of Gamma-Aminobutyric Acid is about 10 mg, about 10 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, or about 500 mg.

In some embodiments, the amount of valyrian root extract is about 1 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, about 140 mg, about 145 mg, about 150 mg, about 155 mg, about 160 mg, about 165 mg, about 170 mg, about 175 mg, about 180 mg, about 185 mg, about 190 mg, or about 200 mg.

In some embodiments, the amount of immediate release melatonin is about 0.1 mg, about 0.15 mg, about 0.2 mg, about 0.25 mg, about 0.3 mg, about 0.35 mg, about 0.4 mg, about 0.45 mg, about 0.5 mg, about 0.55 mg, about 0.6 mg, about 0.65 mg, about 0.7 mg, about 0.75 mg, about 0.8 mg, about 0.85 mg, about 0.9 mg, about 0.95 mg, about 1.0 mg, about 1.05 mg, about 1.1 mg, about 1.15 mg, about 1.2 mg, about 1.25 mg, about 1.3 mg, about 1.35 mg, about 1.4 mg, about 1.45 mg, about 1.5 mg, about 1.55 mg, about 1.6 mg, about 1.65 mg, about 1.7 mg, about 1.75 mg, about 1.8 mg, about 1.85 mg, about 1.9 mg, about 1.95 mg, about 2.0 mg, about 2.05 mg, about 2.1 mg, about 2.15 mg, about 2.2 mg, about 2.25 mg, about 2.3 mg, about 2.35 mg, about 2.4 mg, about 2.45 mg, about 2.5 mg, about 2.55 mg, about 2.6 mg, about 2.65 mg, about 2.7 mg, about 2.75 mg, about 2.8 mg, about 2.85 mg, about 2.9 mg, about 2.95 mg, about 3.0 mg, about 3.05 mg, about 3.1 mg, about 3.15 mg, about 3.2 mg, about 3.25 mg, about 3.3 mg, about 3.35 mg, about 3.4 mg, about 3.45 mg, about 3.5 mg, about 3.55 mg, about 3.6 mg, about 3.65 mg, about 3.7 mg, about 3.75 mg, about 3.8 mg, about 3.85 mg, about 3.9 mg, about 3.95 mg, about 4.0 mg, about 4.05 mg, about 4.1 mg, about 4.15 mg, about 4.2 mg, about 4.25 mg, about 4.3 mg, about 4.35 mg, about 4.4 mg, about 4.45 mg, about 4.5 mg, about 4.55 mg, about 4.6 mg, about 4.65 mg, about 4.7 mg, about 4.75 mg, about 4.8 mg, about 4.85 mg, about 4.9 mg, about 4.95 mg, about 4.0 mg, about 4.05 mg, about 4.1 mg, about 4.15 mg, about 4.2 mg, about 4.25 mg, about 4.3 mg, about 4.35 mg, about 4.4 mg, about 4.45 mg, about 4.5 mg, about 4.55 mg, about 4.6 mg, about 4.65 mg, about 4.7 mg, about 4.75 mg, about 4.8 mg, about 4.85 mg, about 4.9 mg, about 4.95 mg, or about 5.0 mg.

In some embodiments, the amount of delayed release melatonin is about 0.1 mg, about 0.15 mg, about 0.2 mg, about 0.25 mg, about 0.3 mg, about 0.35 mg, about 0.4 mg, about 0.45 mg, about 0.5 mg, about 0.55 mg, about 0.6 mg, about 0.65 mg, about 0.7 mg, about 0.75 mg, about 0.8 mg, about 0.85 mg, about 0.9 mg, about 0.95 mg, about 1.0 mg, about 1.05 mg, about 1.1 mg, about 1.15 mg, about 1.2 mg, about 1.25 mg, about 1.3 mg, about 1.35 mg, about 1.4 mg, about 1.45 mg, about 1.5 mg, about 1.55 mg, about 1.6 mg, about 1.65 mg, about 1.7 mg, about 1.75 mg, about 1.8 mg, about 1.85 mg, about 1.9 mg, about 1.95 mg, about 2.0 mg, about 2.05 mg, about 2.1 mg, about 2.15 mg, about 2.2 mg, about 2.25 mg, about 2.3 mg, about 2.35 mg, about 2.4 mg, about 2.45 mg, about 2.5 mg, about 2.55 mg, about 2.6 mg, about 2.65 mg, about 2.7 mg, about 2.75 mg, about 2.8 mg, about 2.85 mg, about 2.9 mg, about 2.95 mg, about 3.0 mg, about 3.05 mg, about 3.1 mg, about 3.15 mg, about 3.2 mg, about 3.25 mg, about 3.3 mg, about 3.35 mg, about 3.4 mg, about 3.45 mg, about 3.5 mg, about 3.55 mg, about 3.6 mg, about 3.65 mg, about 3.7 mg, about 3.75 mg, about 3.8 mg, about 3.85 mg, about 3.9 mg, about 3.95 mg, about 4.0 mg, about 4.05 mg, about 4.1 mg, about 4.15 mg, about 4.2 mg, about 4.25 mg, about 4.3 mg, about 4.35 mg, about 4.4 mg, about 4.45 mg, about 4.5 mg, about 4.55 mg, about 4.6 mg, about 4.65 mg, about 4.7 mg, about 4.75 mg, about 4.8 mg, about 4.85 mg, about 4.9 mg, about 4.95 mg, about 4.0 mg, about 4.05 mg, about 4.1 mg, about 4.15 mg, about 4.2 mg, about 4.25 mg, about 4.3 mg, about 4.35 mg, about 4.4 mg, about 4.45 mg, about 4.5 mg, about 4.55 mg, about 4.6 mg, about 4.65 mg, about 4.7 mg, about 4.75 mg, about 4.8 mg, about 4.85 mg, about 4.9 mg, about 4.95 mg, or about 5.0 mg.

Nutritional Supplement

In another aspect, described herein is a nutritional supplement comprising:
 (a) a probiotic component;
 (b) a sleep support component;
 (c) at least one excipient; and
 (d) a capsule.

Excipients

In some embodiments, the excipient is selected from sugars, starches, polymers, alkaline and/or alkali earth stearate, carbonate and/or sulfate, kaolin, silica, flavorants, and aromas, and combinations of any thereof. In some embodiments, the excipient may be lipophilic, polymeric, cellulosic or combinations of any thereof. In some embodiments, the excipient may be selected from lactose, magnesium stearate, sodium carbonate, microcrystalline cellulose, silica, titanium dioxide, and combinations of any thereof. In some embodiments, the excipient comprises at least one of microcrystalline cellulose, silica, magnesium stearate, and combinations of any thereof.

In some embodiments, the amount of microcrystalline cellulose is 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, about 40 mg, about 41 mg, about 42 mg, about 43 mg, about 44 mg, about 45 mg, about 46 mg, about 47 mg, about 48 mg, about 49 mg, about 50 mg, about 51 mg, about 52 mg, about 53 mg, about 54 mg, about 55 mg, about 56 mg, about 57 mg, about 58 mg, about 59 mg, about 60 mg, about 61 mg, about 62 mg, about 63 mg, about 64 mg, about 65 mg, about 66 mg, about 67 mg, about 68 mg, about 69 mg, about 70 mg, about 71 mg, about 72 mg, about 73 mg, about 74 mg, about 75 mg, about 76 mg, about 77 mg, about 78 mg, about 79 mg, about 80 mg, about 81 mg, about 82 mg, about 83 mg, about 84 mg, about 85 mg, about 86 mg, about 87 mg, about 88 mg, about 89 mg, about 90 mg, about 91 mg, about 92 mg, about 93 mg, about 94 mg, about 95 mg, about 96 mg, about 97 mg, about 98 mg, about 99 mg, or about 100 mg.

In some embodiments, the amount of silica is 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 11 mg, about 12 mg, about 13 mg, about 14 mg, about 15 mg, about 16 mg, about 17 mg, about 18 mg, about 19 mg, or about 20 mg.

In some embodiments, the amount of magnesium stearate is 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 11 mg, about 12 mg, about 13 mg, about 14 mg, about 15 mg, about 16 mg, about 17 mg, about 18 mg, about 19 mg, or about 20 mg.

According to an embodiment, therapeutic compositions for improving digestion may comprise: a probiotic component, comprising: at least one of *Lactobacillus acidophilus, Bifidobacterium bifidum, Bifidobacterium animalis, Lactobacillus rhamnosus*, and *Lactobacillus paracasei*; and a sleep support component, comprising: at least one of gamma-aminobutyric acid (GABA), valerian root extract, and melatonin. The therapeutic compositions may be further comprising at least on excipient. The excipient may be at least one of microcrystalline cellulose, silica, magnesium stearate, or a combination thereof. The therapeutic composition may comprise a probiotic component comprising: *Lactobacillus acidophilus, Bifidobacterium bifidum, Bifidobacterium animalis* subsp. *lactis, Lactobacillus rhamnosus*, and *Lactobacillus paracasei*; gamma-aminobutyric acid (GABA), valerian root extract, and melatonin. The therapeutic composition may further comprise: microcrystalline cellulose, silica, and magnesium stearate. According to an embodiment, compositions for improving digestion may comprise: a probiotic component comprising: *Lactobacillus acidophilus, Bifidobacterium bifidum, Bifidobacterium animalis* subsp. *lactis, Lactobacillus rhamnosus*, and *Lactobacillus paracasei*; gamma-aminobutyric acid (GABA), valerian root extract, and melatonin. The composition may further comprise at least one of microcrystalline cellulose, silica, magnesium stearate, or a combination thereof. The composition may comprise: at least 0.05 B CFU/g of the probiotic component, at least 10 mg of gamma-aminobutyric acid (GABA), at least 1 mg of valerian root extract, and at least 0.1 mg of melatonin. The composition may comprise from about 0.05 B CFU/g to about 50 B CFU/g of the probiotic component, from about 10 mg to about 500 mg of gamma-aminobutyric acid (GABA), from about 1 mg to about 200 mg of valerian root extract, from about 0.1 mg to about 5 mg of an immediate release melatonin, and from about 0.1 mg to about 5 mg of a delayed release melatonin. The composition may comprise: about 27 B CFU/g of the probiotic component, about 100 mg of gamma-aminobutyric acid (GABA), about 50 mg of valerian root extract, about 0.75 mg of an immediate release melatonin, and about 0.75 mg of a delayed release melatonin.

According to an embodiment, compositions for improving digestion may comprise: a clinical culture blend comprising: *Lactobacillus acidophilus* (ATCC SD6865), *Lactobacillus acidophilus* (ATCC SD6866), *Bifidobacterium bifidum* (ATCC SD6869), and *Bifidobacterium animalis* subsp. *lactis* (ATCC SD6870); an active microbiome blend comprising: *Lactobacillus rhamnosus* (IMC 501), and *Lactobacillus paracasei* (IMC 502); gamma-aminobutyric acid (GABA); valerian root extract; immediate release melatonin; and delayed release melatonin. The composition may further comprise: microcrystalline cellulose, silica, and magnesium stearate. The composition may comprise: at least 1 B CFU/g of the clinical culture blend, at least 0.1 B CFU/g of the active microbiome blend, at least 10 mg of gamma-aminobutyric acid (GABA), at least 1 mg of valerian root extract, at least 0.1 mg of an immediate release melatonin, and at least 0.1 mg of a delayed release melatonin. The composition may comprise: from about 1 B CFU/g to about 50 B CFU/g of the clinical culture blend, from about 0.1 B CFU/g to about 5 B CFU/g of the active microbiome blend, from about 10 mg to about 500 mg of the gamma-aminobutyric acid (GABA), from about 1 mg to about 200 mg of the valerian root extract, from about 0.1 mg to about 5 mg of the immediate release melatonin, and from about 0.1 mg to about 5 mg of the delayed release melatonin. The composition may comprise: about 26 B B CFU/g of the clinical culture blend, about 1 B CFU/g of the active microbiome blend, about 100 mg of the gamma-aminobutyric acid (GABA), about 50 mg of the valerian root extract, about 0.75 mg of the immediate release melatonin, and about 0.75 mg of the delayed release melatonin. The composition may further comprise: about 39 mg microcrystalline cellulose, about 6 mg silica, and about 4 mg magnesium stearate. The composition may be in a capsule.

According to embodiments, methods for improving digestion may comprise administering to an individual an effective dose of a composition comprising: *Lactobacillus acidophilus, Bifidobacterium bifidum, Bifidobacterium animalis* subsp. *lactis, Lactobacillus rhamnosus, Lactobacillus paracasei*, gamma-aminobutyric acid (GABA), valerian root extract, and melatonin. The composition may also promotes sleep. The composition may comprise: about 26 B CFU/g of a clinical culture blend comprising: *Lactobacillus acidophilus* (ATCC SD6865), *Lactobacillus acidophilus* (ATCC SD6866), *Bifidobacterium bifidum* (ATCC SD6869), *Bifidobacterium animalis* subsp. *lactis* (ATCC SD6870); about 1 B CFU/g of an active microbiome blend comprising: *Lactobacillus rhamnosus* (IMC 501), and *Lactobacillus paracasei* (IMC 502); about 100 mg of the gamma-aminobutyric acid (GABA); about 50 mg of the valerian root extract; about 0.75 mg of the immediate release melatonin; and about 0.75 mg of the delayed release melatonin.

EXAMPLES

The following examples are provided for illustrative purposes only, and are intended to be purely exemplary of the disclosure and are not intended to limit the scope of the claims provided herein. Efforts have been made to ensure accuracy with respect to numbers (e.g., amounts, temperature, etc.), but some errors and deviations should be accounted for.

Example 1

| Amount Per Serving | Dosage |
|---|---|
| Active Ingredients | |
| Lab4 ™ Clinical Cultures | 26 B CFU/g |
| *Lactobacillus acidophilus* (ATCC SD6865) | |
| *Lactobacillus acidophilus* (ATCC SD6866) | |
| *Bifidobacterium bifidum* (ATCC SD6869) | |
| *Bifidobacterium animalis* subsp. *lactis* (ATCC SD6870) | |
| Active Microbiome Blend | 1 B CFU/g |
| *Lactobacillus rhamnosus* IMC 501 | |
| *Lactobacillus paracasei* IMC 502 | |
| Gamma-Aminobutyric Acid (from PharmaGABA ®) | 100 mg |
| Valerian Root Extract | 50 mg |
| Melatonin (immediate release) | 0.75 mg |
| Melatonin (delayed release) | 0.75 mg |

-continued

| Amount Per Serving | Dosage |
|---|---|
| Other Ingredients | |
| Microcrystalline Cellulose | 39 mg |
| Silica | 6 mg |
| Magnesium Stearate | 4 mg |
| Capsule | |
| Size "0" Vegetarian HPMC White/Purple Capsule | 1 ea |
| HPMC | 94.0454 mg |
| Titanium Dioxide | 1.92 mg |
| FD&C Red 40 | 0.0269 mg |
| FD&C Blue 1 | 0.0077 mg |

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

What is claimed is:

1. A therapeutic composition for improving digestion consisting of:
    a probiotic component consisting of:
        Lactobacillus acidophilus, Bifidobacterium bifidum, Bifidobacterium animalis, Lactobacillus rhamnosus, and Lactobacilus paracasei;
    a sleep support component consisting of:
        gamma-aminobutyric acid (GABA), valerian root extract, and melatonin; and
    one or more excipients.

2. The therapeutic composition according to claim 1, wherein the excipient is at least one of microcrystalline cellulose, silica, magnesium stearate, or a combination thereof.

3. The therapeutic composition of claim 1, wherein the excipient consists of:
    microcrystalline cellulose,
    silica, and
    magnesium stearate.

4. The therapeutic composition of claim 1, consisting of:
    at least 0.05 B CFU/g of the probiotic component,
    at least 10 mg of gamma-aminobutyric acid (GABA),
    at least 1 mg of valerian root extract, and
    at least 0.1 mg of melatonin; and
    one or more excipients.

5. The therapeutic composition of claim 1, consisting of:
    from about 0.05 B CFU/g to about 50 B CFU/g of the probiotic component,
    from about 10 mg to about 500 mg of gamma-aminobutyric acid (GABA),
    from about 1 mg to about 200 mg of valerian root extract,
    from about 0.1 mg to about 10 mg of melatonin; and
    one or more excipients.

6. The therapeutic composition of claim 1, consisting of:
    about 27 B CFU/g of the probiotic component,
    about 100 mg of gamma-aminobutyric acid (GABA),
    about 50 mg of valerian root extract,
    about 1.50 mg of melatonin; and
    one or more excipients.

7. The composition of claim 1 in a capsule.

8. A composition for improving digestion consisting of:
    a culture blend consisting of:
        Lactobacillus acidophilus (ATCC SD6865),
        Lactobacillus acidophilus (ATCC SD6866),
        Bifidobacterium bifidum (ATCC SD6869), and
        Bifidobacterium animalis subsp. lactis (ATCC SD6870);
    a microbiome blend consisting of:
        Lactobacillus rhamnosus (IMC 501), and
        Lactobacillus paracasei (IMC 502);
    gamma-aminobutyric acid (GABA);
    valerian root extract;
    melatonin; and
    one or more excipients.

9. The composition of claim 8, wherein the one or more excipients consists of:
    microcrystalline cellulose,
    silica, and
    magnesium stearate.

10. The composition of claim 8, consisting of:
    at least 1 B CFU/g of the culture blend,
    at least 0.1 B CFU/g of the microbiome blend,
    at least 10 mg of gamma-aminobutyric acid (GABA),
    at least 1 mg of valerian root extract,
    at least 0.2 mg melatonin, and
    one or more excipients.

11. The composition of claim 8, consisting of:
    from about 1 B CFU/g to about 50 B CFU/g of the culture blend,
    from about 0.1 B CFU/g to about 5 B CFU/g of the microbiome blend,
    from about 10 mg to about 500 mg of the gamma-aminobutyric acid (GABA),
    from about 1 mg to about 200 mg of the valerian root extract,
    from about 0.1 mg to about 10 mg of melatonin; and
    one or more excipients.

12. The composition of claim 11, consisting of:
    about 26 B B CFU/g of the culture blend,
    about 1 B CFU/g of the microbiome blend,
    about 100 mg of the gamma-aminobutyric acid (GABA),
    about 50 mg of the valerian root extract,
    about 01.50 mg of melatonin; and
    one or more excipients.

13. The composition of claim 12, further comprising wherein the one or more excipients consists of:
    about 39 mg microcrystalline cellulose,
    about 6 mg silica, and
    about 4 mg magnesium stearate.

14. A method for improving digestion, comprising administering to an individual an effective dose of a composition consisting of:
    Lactobacillus acidophilus,
    Bifidobacterium bifidum,
    Bifidobacterium animalis subsp. lactis,
    Lactobacillus rhamnosus,
    Lactobacillus paracasei,
    gamma-aminobutyric acid (GABA),
    valerian root extract,
    melatonin; and
    one or more excipients.

15. The method of claim 14, wherein the composition promotes sleep.

16. The method of claim 14, wherein the composition consists of:
- about 26 B CFU/g of a culture blend consisting of:
  - *Lactobacillus acidophilus* (ATCC SD6865),
  - *Lactobacillus acidophilus* (ATCC SD6866),
  - *Bifidobacterium bifidum* (ATCC SD6869), and
  - *Bifidobacterium animalis* subsp. *lactis* (ATCC SD6870);
- about 1 B CFU/g of a microbiome blend consisting of:
  - *Lactobacillus rhamnosus* (IMC 501), and
  - *Lactobacillus paracasei* (IMC 502);
- about 100 mg of the gamma-aminobutyric acid (GABA);
- about 50 mg of the valerian root extract;
- about 1.50 mg of melatonin; and one or more excipients.

* * * * *